United States Patent [19]

Johnson

[11] 4,081,176

[45] Mar. 28, 1978

[54] VALVE FOR AN ORAL EVACUATOR SYSTEM

[76] Inventor: W. Grant Johnson, 717 E. Chapman, Orange, Calif. 92667

[21] Appl. No.: 660,081

[22] Filed: Feb. 23, 1976

Related U.S. Application Data

[63] Continuation-in-part of Ser. No. 592,140, Jul. 1, 1975, Pat. No. 4,015,336.

[51] Int. Cl.² .............................................. F16K 31/00
[52] U.S. Cl. ........................................ 251/342; 32/33; 251/347; 251/348; 251/353; 251/354; 251/321; 128/276
[58] Field of Search .................... 128/274, 276; 32/33; 251/342, 347, 343, 344, 348, 321, 353, 354

[56] References Cited

U.S. PATENT DOCUMENTS

| 2,161,135 | 6/1939 | Chappell | 251/347 |
| 2,208,032 | 7/1940 | Hooper | 128/274 |
| 2,623,787 | 12/1952 | Smith | 251/342 |
| 2,623,790 | 12/1952 | Smith | 251/342 |
| 2,799,471 | 7/1957 | Maroney | 251/342 |
| 3,183,934 | 5/1965 | Miner | 251/342 |
| 3,609,783 | 10/1971 | Cooke | 251/354 |
| 3,971,541 | 7/1976 | Griffin | 251/342 |

FOREIGN PATENT DOCUMENTS

| 965,536 | 4/1948 | France | 251/347 |
| 430,189 | 6/1926 | Germany | 251/347 |
| 373,874 | 3/1939 | Italy | 251/342 |
| 389,957 | 1/1932 | United Kingdom | 128/274 |
| 1,107,560 | 1/1965 | United Kingdom | 251/342 |

Primary Examiner—William R. Cline
Assistant Examiner—H. Jay Spiegel
Attorney, Agent, or Firm—Albert H. Graddis; Jeremiah J. Duggan

[57] ABSTRACT

A specific embodiment provides a valve structure for an evacuator system adapted to be connected to a source of negative pressure. The valve structure includes an elongated housing having a longitudinal bore extending through the housing, and a valve seat formed by a reduced diameter portion of the bore. A valve member is situated in the bore for abutting engagement with the valve seat to prevent passage of flowable materials therebetween. Biasing means is provided for urging the valve member into abutting engagement with the valve seat. A manually operable member is operatively associated with the biasing means for moving the valve member out of engagement with the valve seat to permit passage of flowable materials therebetween.

5 Claims, 11 Drawing Figures

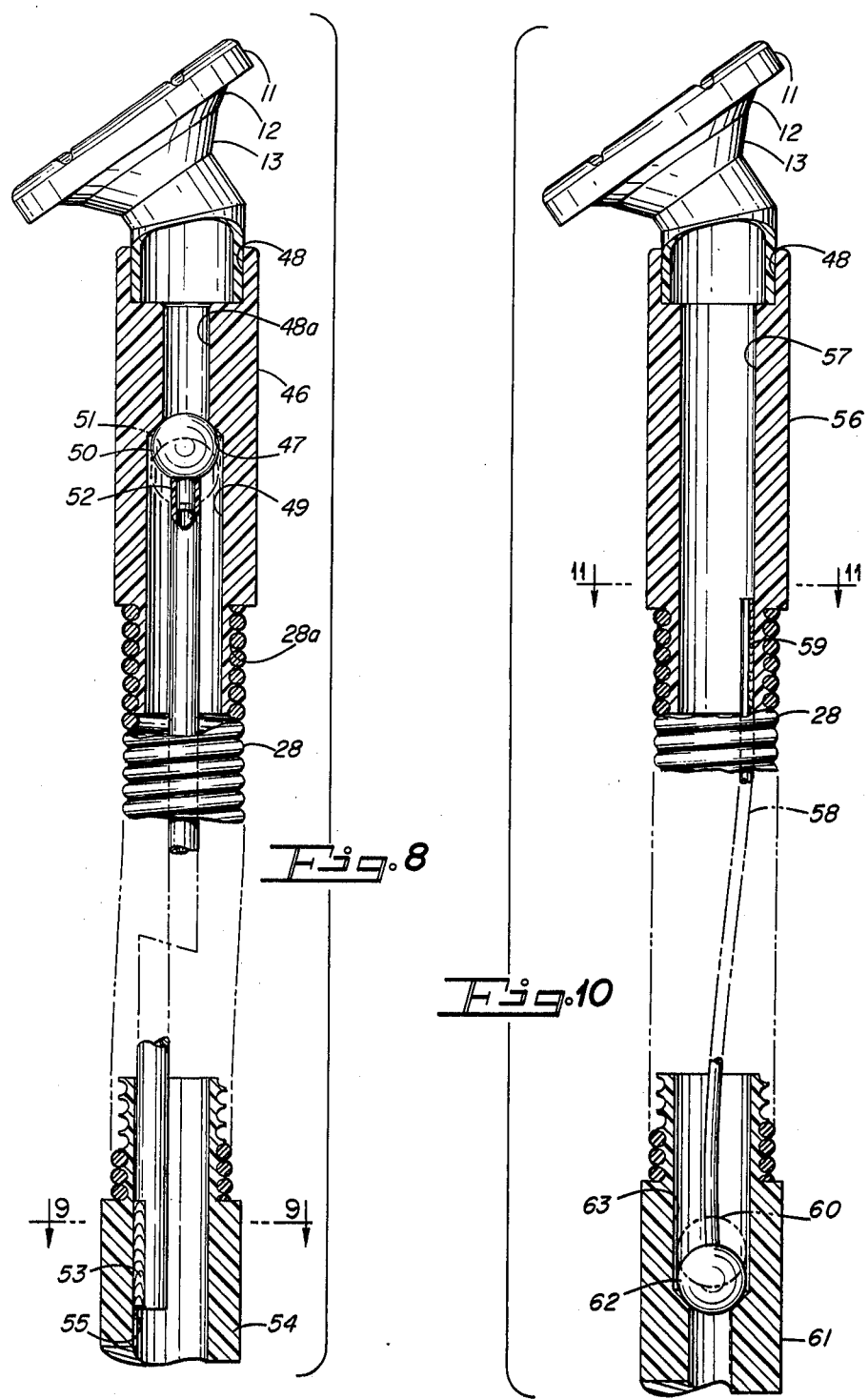

VALVE FOR AN ORAL EVACUATOR SYSTEM

This application is a continuation-in-part of our co-pending application Ser. No. 592,140, filed July 1, 1975, now U.S. Pat. No. 4,015,336.

BACKGROUND OF THE INVENTION

The present invention relates to a valve structure for an evacuator system. Particularly, the present invention finds use in the valve structure of an oral evacuator system.

While being treated by a dentist, a patient is frequently required to lean from the dental chair to rinse his mouth. U.S. Pat. No. 3,742,607 discloses an oral evacuator system which provides a hand-held assembly connected to a vacuum source which is brought to the mouth of a patient to cleanse rinsing water and other flowable materials therefrom.

SUMMARY OF THE INVENTION

The present invention provides a valve structure for an evacuator system. In accordance with the present invention there is provided a valve structure for an evacuator system adapted to be connected to a source of negative pressure. The valve structure includes an elongated housing having a longitudinal bore extending through the housing, a valve seat formed by a reduced diameter portion of the bore. A valve member is situated in the bore for abutting engagement with the valve seat to prevent passage of flowable materials therebetween. A spring is provided for biasing the valve member into abutting engagement with the valve seat. A manually operable member is connected to the spring for moving the valve member out of engagement with the valve seat to permit passage of flowable materials therebetween.

According to another aspect of the invention, resiliently extensible hose means is connected to the source of negative pressure. A valve is operatively associated with the hose means and is normally in a closed position so as to prevent communicating the negative pressure. Means is affixed to the valve means and the hose means to open the valve means when the hose means is extended beyond a pre-determined axial length.

BRIEF DESCRIPTION OF THE DRAWINGS

FIG. 8 is a side elevational, partial, cross-sectional view of another valve structure embodiment.

FIG. 9 is a cross-sectional plan view of a portion of the embodiment of FIG. 8.

FIG. 10 is a side elevational, partial, cross-sectional view of another valve structure embodiment.

FIG. 11 is a cross-sectional view of a portion of the embodiment of FIG. 10.

DESCRIPTION OF SPECIFIC EMBODIMENTS

Figure 1:
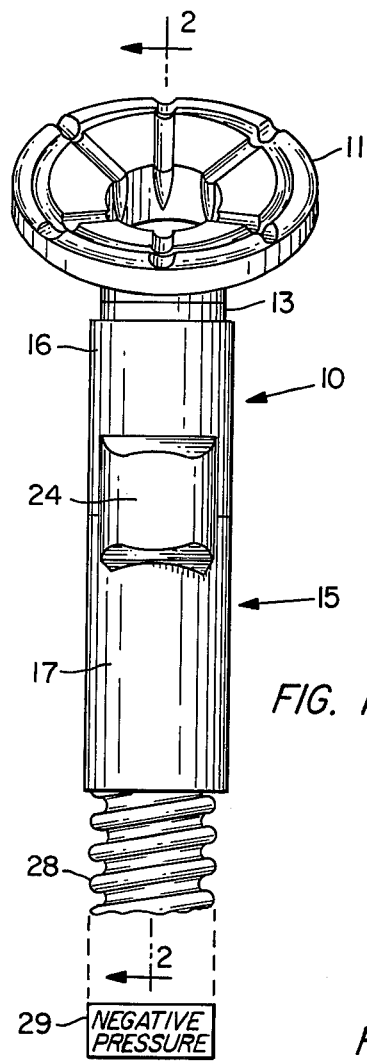
FIG. 1 is a front elevational view of a hand-held portion of an oral evacuator system.
Figure 3:
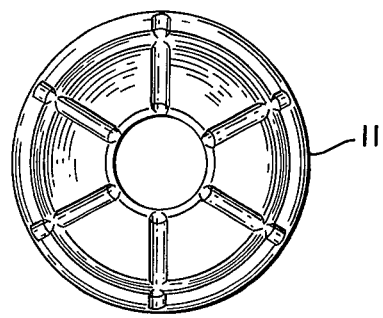
FIG. 3 is a top plan view of a replaceable and disposable mouthpiece of the hand-held portion of the system shown in FIG. 1.

With reference to FIGS. 1-6, a hand-held portion 10 of an oral evacuation system has a replaceable mouthpiece 11 at the upper end thereof. The mouthpiece 11 is fitted about an outwardly flared end 12 of head member 13. The head member 13 is frictionally seated in the upper portion of a bore 14 formed in a housing 15. The housing 15 has an upper member 16 threaded at the lower end thereof for threading engagement with a lower member 17.

A valve seat 18 is formed in the lower member 17 of the housing 15 by a reduced diameter portion of the bore 14. A valve member 20 is positioned in the bore 14 in abutting engagement with the valve seat 18, and a spring 21 is connected to the valve member 20 at the lower end thereof and in abutting engagement with a shoulder 22 formed in a bore 14 to bias the valve member 20 into an abutting engagement with the valve seat 18.

The spring 21 has an offset looped portion 23 extending outwardly through a slot 19 in the upper member 16. A finger engageable member 24 is connected to the offset looped portion 23 by a pin 25 extending transversely through the finger operable member 25 and beneath the looped portion 23.

The bottom of the lower member 17 has a reduced diameter portion 26 extending outwardly from annulus 27. The reduced diameter portion 26 is fitted into a flexible hose 28 which is seated in the annulus 27. The downstream end of the hose 28 is connected to a source of negative pressure 29. The negative pressure source 29 must be of sufficient vacuum to draw flowable materials from the mouth of a patient into the head 13, and through the bore 14 and between the valve member 20 and valve seat 18 to the interior of the hose 28. For example, the negative pressure may be a vacuum in the order of 4 to 6 p.s.i. less than atmospheric pressure.

Figure 6:
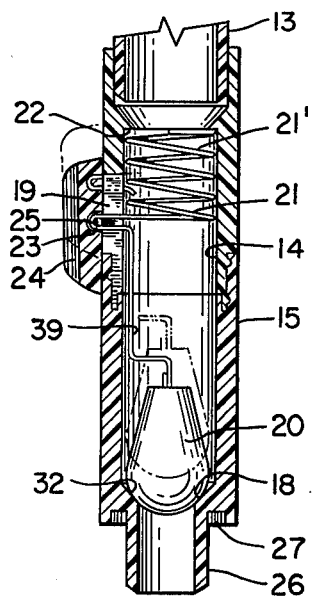
FIG. 6 is a cross-sectional view of the valve structure embodiment of FIG. 2 with the components assembled.

The manually operable member 24 and offset spring portion 23 are movable upwardly in the slot 19 to the position shown in dashed lines in FIG. 6 to compress the spiral portion of the spring 21 and lift the valve member 20 upstream out of engagement with the valve seat 18. The patient or dentist may hold the manually operable member 24 in this position to evacuate flowable materials from the patient's mouth. Alternatively, the valve structure can be locked in an opened position by positioning the offset portion 23 in a transverse portion 30 (FIG. 5) of the slot 19. The transverse slot portion 30 extends downwardly a slight distance at 31 (FIG. 5) to seat the offset portion 23 therein. Thus, to close the valve assembly, the manually operable member 24 is first moved upwardly to lift the offset portion 23 out of seating engagement in the transverse slot portion 30. Then the manually operable member is moved transversely to the left, as viewed in FIG. 5, to position the offset portion 30 in the longitudinal position of the slot 19. Thereafter, the bias of the spring 21 moves the valve member 20 into seating engagement with the valve seat 18 to prevent passage of flowable materials therebetween. The bore 14 is beveled 32 to guide the valve member 20 into the engagement with the valve seat 18.

The manually operable member 24 is dimensioned to cover the slot 19, including the transverse slot portion 23, irrespective of the position of the offset spring portion 23 in the slot 19. By covering the slot 19 throughout operation of the valve structure, the loss of negative pressure of the slot 19 is reduced or immunized.

Figure 2:
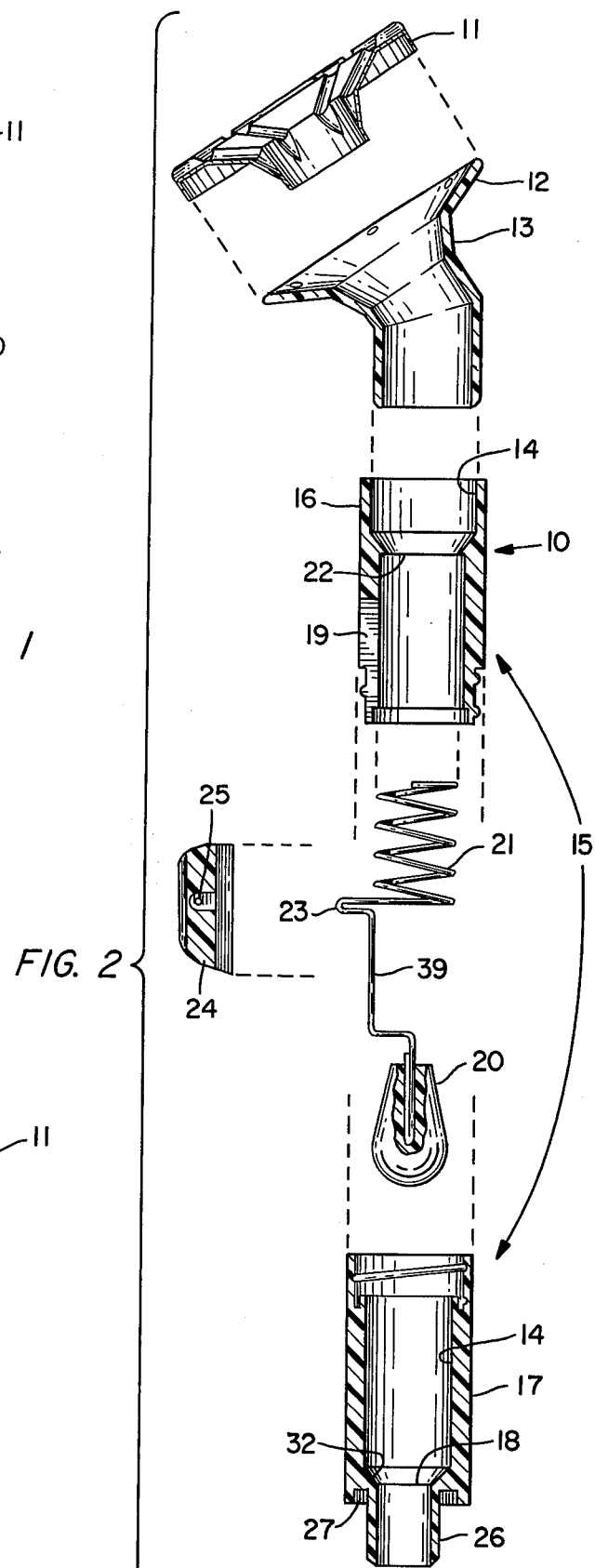
FIG. 2 is an exploded cross-sectional view taken along lines 2—2 of FIG. 1.
Figure 4:
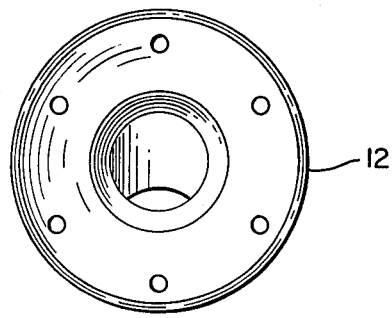
FIG. 4 is a top plan view of a removable head of the hand-held portion shown in FIG. 1.
Figure 5:
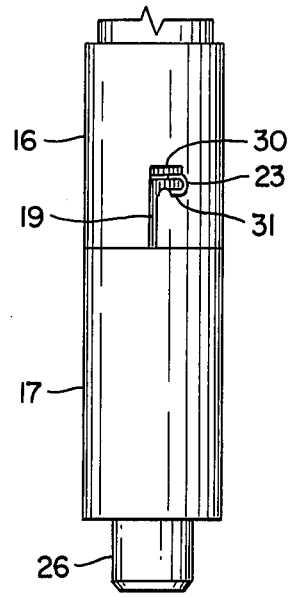
FIG. 5 is a side elevational view of a portion of FIG. 1 with a finger operable member removed.

In the embodiment shown in FIGS. 2 and 6, the offset spring portion 23 is formed between the spiral portion 21 upstream of the valve member 20 in the extension 39 of the spring 21 that is connected to the valve member 20. By positioning the spring 21 and the valve member 20 upstream of the valve seat 18, the negative pressure source 29 aids the spring 21 in maintaining the valve member 20 in abutting engagement with the valve seat.

Obviously, the valve member 20 and the spring 21 may be situated downstream of the valve seat 18, but, in this case, the negative pressure source 29 would pull against the bias of the spring 21 to tend to move the valve member 20 out of engagement with the valve seat 18.

Figure 7:
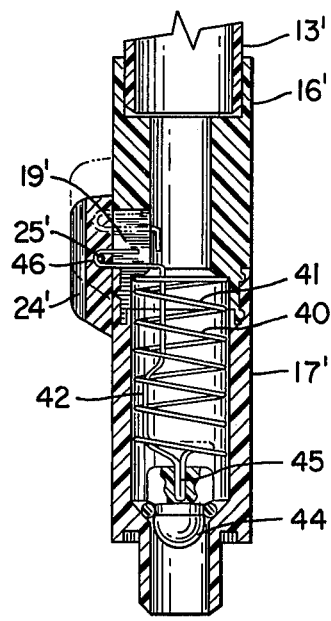
FIG. 7 is a cross-sectional view of another valve structure embodiment.

In an alternative embodiment shown in FIG. 7, the spring 40 has an extension 42 connected at 45 to the valve member 44 downstream of the spiral portion 41. The extension 42 is folded back through the spiral portion 41, and the offset spring portion 46 is at the upper end of the extension 42 upstream of the spiral portion 41. As in the embodiment of FIGS. 2 and 6, the offset spring portion 46 extends through the slot 19' in the upper member 16' and is connected to the manual or finger-operable member 24' by the pin 25'.

Referring to FIG. 8, an embodiment of the present invention is shown. Housing or end fitting 46 is frictionally affixed to an assembly, comprising head member 13, flared-end member 12, and mouthpiece 11. Fitting 46 is essentially a hollow cylindrical member having an internal bore communicating and in registration with head member 13. The internal bore of fitting 46 consists of three portions of varying diametrical dimension. First, portion 48 mates with head member 13 and is dimensionally controlled so as to be in frictional contact therewith. A second narrower bore portion 48a extends concentrically from portion 48 opening into a thrid and last bore portion 49 having again increased diameter. A fusto-concial transitional zone, interconnecting portions 48a and 49, forms a valve seat 47. While the present embodiment incorporates valve seat 47 as a conic section, it of course may be spherical or even ellipsoidal in shape if such be desirable and consonant with overall design and function of the valve.

Threaded end 28a of fitting 46 connects to a flexible resiliently extensible hose 28 for communicating a negative pressure. Hose 28 comprising a helically wound spring member encased in a suitable plastic or rubber material of a type well known in the art, is of selected diameter and has an axial length sufficient to provide necessary manipulation. One end of hose 28 is threadably engaged to portion 28a of fitting 26 while its other end is similarly engaged to a second fitting 54. Fitting 54 again essentially of cylindrical geometry has an internal bore 55 which connects to the source of negative pressure.

Internally of the hose means assembly comprising fitting 54 and hose 28 is located a tubular wand member 52 extending axially therein. One end 53 of wand 52 is affixed to and internally of bore 53. Referring to FIG. 9, these members may be connected by cementing, ultrasonic welding 56 or whatever means found suitable to the design of the structure. Wand 52 extends axially through hose 28 where at its distal end it is attached to a valve member or poppet 50. Valve member 50 is affixed internally of wand 52 by means of pin member 51 extending therefrom. Member 51 may be affixed to wand 52 by press-sitting therein, or any other method providing sufficient structural integrity and may comprise an integrally molded structure. In the normal non-use unextended condition of hose 28, valve member 50 is maintained in abutting engagement with valve seat 47 by the force exerted thereon through wand 52. Wand 52 is designed to have sufficient axial stiffness and length so as to maintain valve member 50 in engagement with valve seat 47, thereby preventing communication of the negative pressure from fitting 54 through hose 28 to head member 13.

When in use, fitting 46 is grasped and extended. As the axial length of hose 28 is urged beyond a predetermined distance, valve member 50 is withdrawn from abutting engagement with valve seat 47 and communication is established between mouthpiece 11 and the source of negative pressure connecting to fitting 54. As long as the assembly is maintained in this extended condition, any fluid or debris placed within or about mouthpiece 11 is drawn therein and through hose 28 into the source of negative pressure. Thus is provided an evacuator system which is automatically actuated upon extension of the mouthpiece 11, and again automatically shut-off upon return of the assembly to its normal non-operating condition.

Yet another form of the present invention is illustrated in FIG. 11. A fitting 56 having an internal bore 57 communicates with and is attached to head member 13 and in turn flared-end 12 and mouthpiece 11. Its other end threadably engages flexible extensible hose 28 which in turn is connected to an threadably engaged on a second fitting 61.

Fitting 61 having substantially cylindrical shape is connected to the source of negative pressure and has an internal bore communicating therethrough. A first bore portion 63 connecting with hose 28 interconnects with a second bore portion 64 of narrower diameter through a transitional, fusto-conical section or valve seat 62. Valve seat 62 mates with, and is in abutting engagement with, a spherical poppet or valve member 60. Valve member 60 includes a wand member 58 to which it is affixed which wand 58 extends from spherical valve member 60 axially of hose 28 connecting to bore 57 of fitting 56 at its distal end.

Referring to FIG. 11, as in the case of the embodiment contained in FIG. 8, wand 58 may be connected to bore 57 by ultrasonic welding 59 or any other means normally applicable to the joining of such members. As head member 13 is extended, and hose 28 urged beyond a certain predetermined axial length, valve member 60 is lifted from its normal abutting engagement with valve seat 62, thereby permitting communication between the source of negative pressure and mouthpiece 11. In this extended state, debris and fluids are transmitted from mouthpiece 11 through hose 28 and into the source of negative pressure. In this embodiment wand 58 may be relatively flexible in that when the assembly is returned to its normal or unextended state, the abutting engagement between valve member 60 and valve seat 62 is maintained by the force exerted by normal atmospheric pressure. In other words, differential force established on valve member 60 by means of the negative pressure tends to maintain proper engagement of the valve, thereby minimizing any additional forces necessary to the maintenance of a sealed condition.

The drawings when considered with the foregoing description of the present invention have described a novel evacuator system adapted to communicate a source of negative pressure to a patient or user. The system includes a flexible, resiliently extensible hose means connected to the source of negative pressure. A fitting member affixed to one end of the hose means and a valve seat formed internally thereof. The valve member or poppet is operatively associated with the valve seat and is normally in abutting engagement therewith, thereby preventing communicating the negative pressure to the user. A wand member is connected to the valve poppet and internally of the hose means. When the hose means is extended by the user beyond a predetermined axial length, the wand member acts to retract the valve member or poppet from engagement with the valve seat and thus communicates the negative pressure to the user permitting disposal of excessive fluid and debris.

While the embodiments of the present invention have been illustrated as cooperating with a dental mouthpiece, operation with other vacuum instruments is completely compatible with its design. Thus, those modifications which are obvious to one of ordinary skill in the art are considered to be within the scope of the present invention as set out in the claims.

What is claimed is:

1. An evacutor system adapted to communicate a negative pressure comprising:
   a flexible axially resilient extensible hose member connected to the negative pressure; the hose member being radially bendable;
   a first fitting member affixed to one end of the hose member having an internal bore for communicating the negative pressure and a valve seat located therein;
   a valve poppet member operatively associated with the hose member normally in abutting sealed engagement with the valve seat; and
   an axially stiff radially flexible wand member having one end connected to the valve poppet member and another end affixed to a second fitting member at another end of the hose member to retract the valve poppet member from abutting engagement with the valve seat only upon axial extension of the hose member.

2. The system of claim 1 wherein the wand member is a tubular member of selected axial length and stiffness and extends internally of the hose member.

3. The system of claim 2 wherein the fitting members threadably engage the hose member; the hose member includes a helically wound spring member extending the entire axial length; the valve seat is of conic geometry; and te valve member is a valve poppet of substantially spherical geometry.

4. The system of claim 2 wherein the wand member and the valve member comprise an integrally molded structure.

5. The system of claim 1 wherein the fitting member is adapted to be removably affixed to the negative pressure and the valve member is urged in to abutting engagement with the valve seat by the negative pressure.

* * * * *